(12) United States Patent
Di Clemente-Besse et al.

(10) Patent No.: US 10,774,142 B2
(45) Date of Patent: Sep. 15, 2020

(54) ANTI-MULLERIAN HORMONE (AMH) NEUTRALIZING ANTIBODIES AND USES THEREOF

(71) Applicants: INSERM (INSTITUT NATIONAL DE LA SANTÉET DE LA RECHERCHE MÉDICALE), Paris (FR); CENTRE NATIONAL DE LA RECHERCHE SCIENTIFIUQUE (CNRS); UNIVERSITÉPARIS DIDEROT—PARIS 7, Paris (FR); UNIVERSITÉPARIS-SUD, Orsay (FR)

(72) Inventors: Nathalie Di Clemente-Besse, Paris (FR); Nathalie Josso, Montrouge (FR); Richard Cate, Paris (FR); Corinne Belville, Montrouge (FR)

(73) Assignees: INSERM (INSTITUT NATIONAL DE LA SANTE ET DE LA RECHERCHE MEDICALE), Paris (FR); CENTRE NATIONAL DE LA RECHERCHE SCIENTIFIQUE (CNRS), Paris (FR); UNIVERSITE PARIS DIDEROT—PARIS 7, Paris (FR); UNIVERSITE PARIS—SUD, Orsay (FR)

( * ) Notice: Subject to any disclaimer, the term of this patent is extended or adjusted under 35 U.S.C. 154(b) by 0 days.

(21) Appl. No.: 15/761,240

(22) PCT Filed: Sep. 23, 2016

(86) PCT No.: PCT/EP2016/072704
§ 371 (c)(1),
(2) Date: Mar. 19, 2018

(87) PCT Pub. No.: WO2017/050974
PCT Pub. Date: Mar. 30, 2017

(65) Prior Publication Data
US 2018/0258167 A1    Sep. 13, 2018

(30) Foreign Application Priority Data
Sep. 25, 2015 (EP) .................................. 15306492

(51) Int. Cl.
*C07K 16/26* (2006.01)

(52) U.S. Cl.
CPC .......... *C07K 16/26* (2013.01); *C07K 2317/20* (2013.01); *C07K 2317/21* (2013.01); *C07K 2317/24* (2013.01); *C07K 2317/565* (2013.01); *C07K 2317/76* (2013.01)

(58) Field of Classification Search
None
See application file for complete search history.

(56) References Cited

U.S. PATENT DOCUMENTS 5,010,055 A    4/1991    Donahoe

FOREIGN PATENT DOCUMENTS

| EP | 1 074 265 A1 | 2/2001 |
| EP | 2 161 579 A1 | 3/2010 |
| WO | 2008/153433 A1 | 12/2008 |
| WO | 2014/074835 A2 | 5/2014 |

OTHER PUBLICATIONS

Long et al., J Clin Endocrinol Metab, 2000; 85: 540-544 (Year: 2000).*
Amer et al., Human Reproduction, 2009; 24: 2760-2766 (Year: 2009).*
Di Clemente et al, "Processing of Anti-Muellerian Hormone Regulates Receptor Activation by a Mechanism Distinct from TGF-[beta]", Molecular Endocrinology, Nov. 1, 2010, pp. 2193-2206, vol. 24, No. 11.
Wilson et al., "Mullerian inhibiting substance requires its N-terminal domain for maintenance of biological activity, a novel finding within the transforming growth factor-beta family", Molecular Endocrinology, Jan. 1, 1993, pp. 247-257, vol. 7, No. 2.

* cited by examiner

*Primary Examiner* — Christina M Borgeest
(74) *Attorney, Agent, or Firm* — W&C IP

(57) ABSTRACT

The present invention relates to Anti-Mullerian Hormone (AMH) neutralizing antibodies and their use in the field of reproduction.

13 Claims, 4 Drawing Sheets

ANTI-MULLERIAN HORMONE (AMH) NEUTRALIZING ANTIBODIES AND USES THEREOF

FIELD OF THE INVENTION

Figure 1:
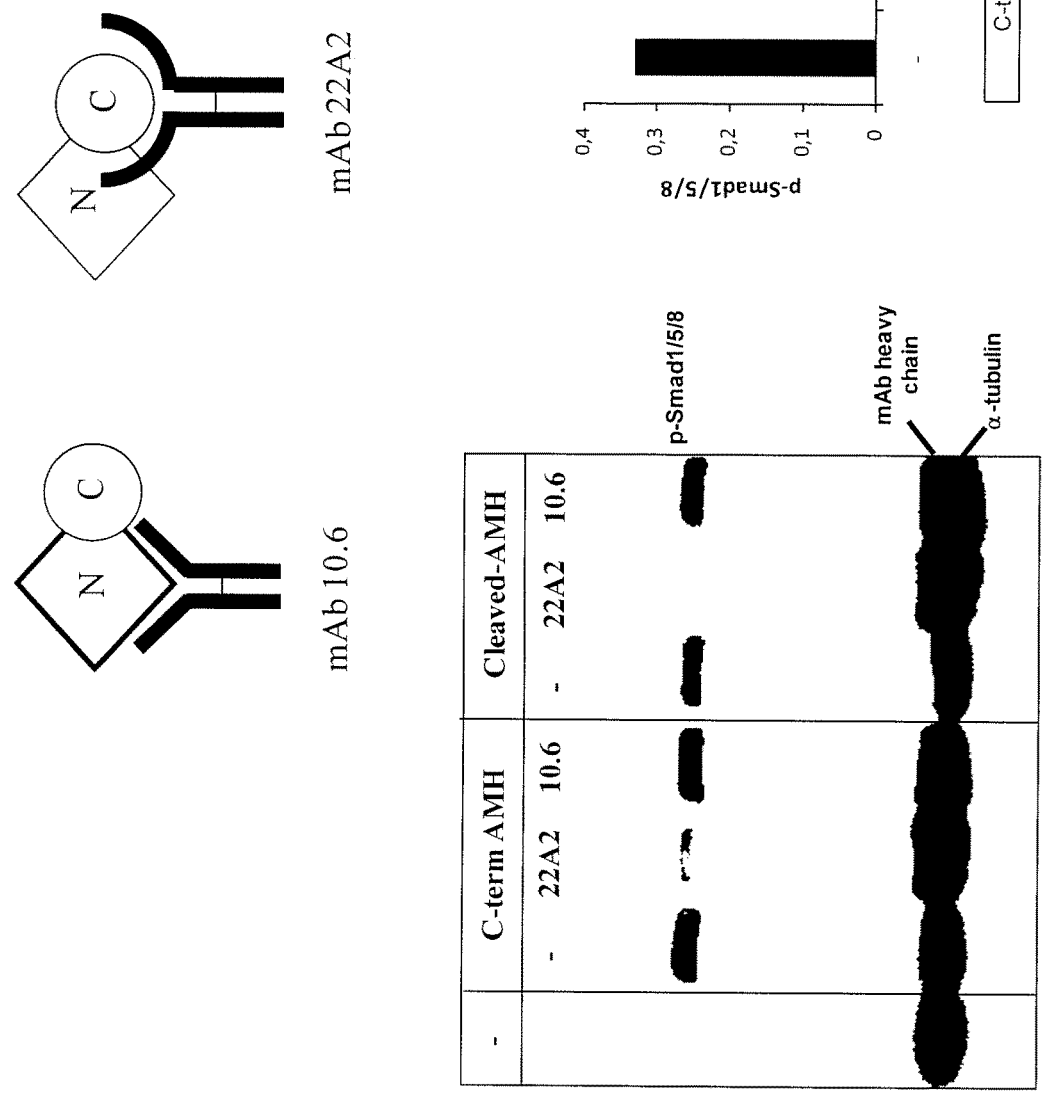

The present invention relates to Anti-Mullerian Hormone (AMH) neutralizing antibodies and their use in the field of reproduction.

BACKGROUND OF THE INVENTION

Anti-Mullerian Hormone (AMH), a member of the Transforming Growth Factor (TGF)-beta family, has important roles in normal male and female reproductive development. In addition, AMH has clinical applications in reproductive endocrinology and potentially oncology, which has focused attention on the AMH signal transduction pathway, with the goal of identifying new approaches for therapeutic intervention and diagnostics. Like other members of the TGF-beta family, AMH signals by assembling a transmembrane serine/threonine kinase receptor complex of type I and type II components, resulting in the phosphorylation and activation of type I receptor kinase by the constitutively active kinase domain of the type II receptor. The activated type I receptor then phosphorylates the cytoplasmic Smad proteins 1, 5, or 8, which migrate into the nucleus and, in concert with other transcription factors, regulate responsive genes. AMHRII, the type II receptor, and AMH, are mutually specific, while ALKs 2, 3 and 6 serve as type I receptors for both AMH and members of the Bone Morphogenetic Protein (BMP) family. AMH is translated as a homodimeric precursor, containing an N-terminal pro-region and a smaller C-terminal mature domain. The precursor undergoes an obligatory cleavage at monobasic sites between the two domains, but the pro-region and C-terminal homodimers remain associated in a noncovalent complex. Unlike other TGF-β ligands, the noncovalent complex can bind to AMHRII, which induces dissociation of the pro-region.

In the male vertebrate embryo, AMH is responsible for the regression of Mullerian ducts, the anlagen of the uterus, Fallopian tubes, and upper part of the vagina. In the adult male, AMH plays a role in Leydig cell differentiation and function. In females, the role of AMH has been predominantly elucidated in rodents, where it has been shown to have an inhibitory effect on primordial follicle recruitment as well as on the responsiveness of growing follicles to Follicle-Stimulating Hormone (FSH). In addition to its role in normal reproductive physiology, AMH is now recognized as an important clinical marker for diagnosing and assessing reproductive disorders. In females, the serum AMH level is indeed a reliable marker for the size of the ovarian follicle pool and a predictor of the ovarian response to controlled ovarian hyperstimulation.

SUMMARY OF THE INVENTION

The present invention relates to Anti-Mullerian Hormone (AMH) neutralizing antibodies and their use in the field of reproduction. In particular, the present invention is defined by the claims.

DETAILED DESCRIPTION OF THE INVENTION

The present invention gives a publicly available source of the specific monoclonal antibody described in J Clin Endocrinol Metab. 2000 February; 85(2):540-4, which is referred by the inventors as mAb 22A2. Indeed, a mAb 22A2 producing hybridoma has been deposited at the Collection Nationale de Cultures de Microorganismes (CNCM, Institut Pasteur, 25 rue du Docteur Roux, 75724 Paris Cedex 15, France), in accordance with the terms of Budapest Treaty, on Apr. 7, 2015. The deposited hybridoma has CNCM deposit number I-4965. The inventors have further characterized the 22A2 antibody and demonstrate that said antibody is capable of neutralizing the activity of AMH on AMHRII. Thus the present invention provides Anti-Mullerian Hormone (AMH) neutralizing antibodies deriving from the 22A2 antibody and their use in the field of reproduction.

As used herein, the term "Anti-Müllerian Hormone" (AMH) corresponds to a 140 kDa glycoprotein hormone. AMH is synthesized as a large precursor with a short signal sequence followed by the pre-pro hormone that forms homodimers. Prior to secretion, the mature hormone undergoes glycosylation and dimerisation to produce a 140-kDa dimer of identical disulphide-linked 70-kDa monomer subunits; each monomer contains an N-terminal domain (also called the "pro" region) and a C-terminal domain (also called the "mature" region). "Uncleaved AMH" as used herein corresponds to the 140-kDa dimer of identical disulphide-linked 70-kDa monomer subunits; each monomer contains an N-terminal domain (also called the "pro" region) and a C-terminal domain (also called the "mature" region). Approximately 10% of AMH produced in cells and secreted into the medium is cleaved at monobasic sites to generate 110-kDa N-terminal and 25-kDa C-terminal homodimers which remain associated in a non-covalent complex. Thus "secreted AMH", as used herein contains about 90% 140 kDa homodimer and about 10% cleaved non-covalent complex. "Bioactive cleaved AMH" as used herein corresponds to the 110-kDa N-terminal and 25-kDa C-terminal homodimers which remain associated in a non-covalent complex, as defined in Pepinsky et al., 1988. "N-terminal AMH" as used herein corresponds to the 110-kDa N-terminal homodimer, as defined in Pepinsky et al., 1988. "C-terminal AMH" as used herein corresponds to the 25-kDa C-terminal homodimer, as defined in Pepinsky et al., 1988. As shown in Pepinsky et al. 1988, uncleaved AMH can be converted to completely bioactive cleaved AMH by treatment with the protease plasmin.

As used herein the term "antibody" or "immunoglobulin" have the same meaning, and will be used equally in the present invention. The term "antibody" as used herein refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments as well as variants (including derivatives) of antibodies and antibody fragments. In natural antibodies, two heavy chains are linked to each other by disulfide bonds and each heavy chain is linked to a light chain by a disulfide bond. There are two types of light chain, lambda (l) and kappa (κ). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CHI, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) can participate to the antibody binding site or influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, typically includes six CDRs, comprising the CDR set from each of a heavy and a light chain V region. Framework Regions (FRs) refer to amino acid sequences interposed between CDRs. The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al."). This numbering system is used in the present specification. The Kabat residue designations do not always correspond directly with the linear numbering of the amino acid residues in SEQ ID sequences. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence. The CDRs of the heavy chain variable domain are located at residues 31-35B (H-CDR1), residues 50-65 (H-CDR2) and residues 95-102 (H-CDR3) according to the Kabat numbering system. The CDRs of the light chain variable domain are located at residues 24-34 (L-CDR1), residues 50-56 (L-CDR2) and residues 89-97 (L-CDR3) according to the Kabat numbering system.

In some embodiments, the antibody of the present invention comprises a heavy chain comprising the H-CDR1, H-CDR2 and H-CDR3 of the heavy chain of the antibody obtainable from the hybridoma available under CNCM deposit number I-4965 and a light chain comprising the L-CDR1, L-CDR2 and L-CDR3 of the light chain of the antibody obtainable from the hybridoma available under CNCM deposit number I-4965.

In some embodiments, the antibody of the present invention comprises the heavy chain of the antibody obtainable from the hybridoma available under CNCM deposit number I-4965 and the light chain of the antibody obtainable from the hybridoma available under CNCM deposit number I-4965.

In some embodiments, the antibody of the present invention is a murine antibody. In particular, said murine antibody may be obtainable from the hybridoma available under CNCM deposit number I-4965.

In some embodiments, the antibody of the present invention is a chimeric antibody, typically a chimeric mouse/human antibody. The term "chimeric antibody" refers to a monoclonal antibody which comprises a VH domain and a VL domain of an antibody derived from a non-human animal, a CH domain and a CL domain of a human antibody. As the non-human animal, any animal such as mouse, rat, hamster, rabbit or the like can be used. In particular, said mouse/human chimeric antibody may comprise the heavy chain and the light chain of the antibody obtainable from hybridoma deposited as CNCM-I-4965.

In some embodiments, the antibody of the present invention is a humanized antibody. As used herein the term "humanized antibody" refers to antibodies in which the framework or "complementarity determining regions" (CDR) have been modified to comprise the CDR from a donor immunoglobulin of different specificity as compared to that of the parent immunoglobulin. In a preferred embodiment, a mouse CDR is grafted into the framework region of a human antibody to prepare the "humanized antibody".

In some embodiments, the antibody of the present invention is selected from the group of Fab, F(ab')2, Fab' and scFv. As used herein, the term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond. The term "F(ab')2" refers to an antibody fragment having a molecular weight of about 100,000 and antigen binding activity, which is slightly larger than the Fab bound via a disulfide bond of the hinge region, among fragments obtained by treating IgG with a protease, pepsin. The term "Fab'" refers to an antibody fragment having a molecular weight of about 50,000 and antigen binding activity, which is obtained by cutting a disulfide bond of the hinge region of the F(ab')2. A single chain Fv ("scFv") polypeptide is a covalently linked VH::VL heterodimer which is usually expressed from a gene fusion including VH and VL encoding genes linked by a peptide-encoding linker. The human scFv fragment of the invention includes CDRs that are held in appropriate conformation, preferably by using gene recombination techniques.

The antibodies of the present invention are produced by any technique known in the art, such as, without limitation, any chemical, biological, genetic or enzymatic technique, either alone or in combination. Typically, knowing the amino acid sequence of the desired sequence, one skilled in the art can readily produce said antibodies, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, antibodies of the present invention can be synthesized by recombinant DNA techniques well-known in the art. For example, antibodies can be obtained as DNA expression products after incorporation of DNA sequences encoding the antibodies into expression vectors and introduction of such vectors into suitable eukaryotic or prokaryotic hosts that will express the desired antibodies, from which they can be later isolated using well-known techniques.

Accordingly, a further object of the invention relates to a nucleic acid molecule encoding an antibody according to the invention. More particularly the nucleic acid molecule encodes a heavy chain or a light chain of an antibody of the present invention.

Typically, said nucleic acid is a DNA or RNA molecule, which may be included in any suitable vector, such as a plasmid, cosmid, episome, artificial chromosome, phage or a viral vector. As used herein, the terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. So, a further object of the invention relates to a vector comprising a nucleic acid of the invention. Such vectors may comprise regulatory elements, such as a promoter, enhancer, terminator and the like, to cause or direct expression of said antibody upon administration to a subject. Examples of promoters and enhancers used in the expression vector for animal cell include early promoter and enhancer of SV40, LTR promoter and enhancer of Moloney mouse leukemia virus, promoter and enhancer of immunoglobulin H chain and the like. ny expression vector for animal cell can be used, so long as a gene encoding the human antibody C region can be inserted and expressed. Examples of suitable vectors include pAGE107, pAGE103, pHSG274, pKCR, pSG1 beta d2-4 and the like. Other examples of plasmids include replicating plasmids comprising an origin of replication, or integrative plasmids, such as for instance pUC, pcDNA, pBR, and the like. Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. Nos. 5,882,877, 6,013,516, 4,861,719, 5,278,056 and WO 94/19478.

A further object of the present invention relates to a host cell which has been transfected, infected or transformed by a nucleic acid and/or a vector according to the invention. As used herein, the term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed".

The nucleic acids of the invention may be used to produce an antibody of the present invention in a suitable expression system. The term "expression system" means a host cell and compatible vector under suitable conditions, e.g. for the expression of a protein coded for by foreign DNA carried by the vector and introduced to the host cell. Common expression systems include E. coli host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include E. coli, Kluyveromyces or Saccharomyces yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective (Urlaub G et al; 1980), rat YB2/3HL.P2.G11.16Ag.20 cell (ATCC CRL1662, hereinafter referred to as "YB2/0 cell"), and the like. The present invention also relates to a method of producing a recombinant host cell expressing an antibody according to the invention, said method comprising the steps of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody. Such recombinant host cells can be used for the production of antibodies of the present invention.

In some embodiments, the method comprises the steps of (i) culturing the hybridoma deposited as CNCM-I-4965 under conditions suitable to allow expression of 22A2 antibody; and (ii) recovering the expressed antibody.

Antibodies of the present invention are suitably separated from the culture medium by conventional immunoglobulin purification procedures such as, for example, protein A-Sepharose, hydroxylapatite chromatography, gel electrophoresis, dialysis, or affinity chromatography.

In some embodiments, the human chimeric antibody of the present invention can be produced by obtaining nucleic sequences encoding VL and VH domains as previously described, constructing a human chimeric antibody expression vector by inserting them into an expression vector for animal cell having genes encoding human antibody CH and human antibody CL, and expressing the coding sequence by introducing the expression vector into an animal cell. As the CH domain of a human chimeric antibody, it may be any region which belongs to human immunoglobulin, but those of IgG class are suitable and any one of subclasses belonging to IgG class, such as IgG1, IgG2, IgG3 and IgG4, can also be used. Also, as the CL of a human chimeric antibody, it may be any region which belongs to Ig, and those of kappa class or lambda class can be used. Methods for producing chimeric antibodies involve conventional recombinant DNA and gene transfection techniques are well known in the art (See Morrison S L. et al. (1984) and patent documents U.S. Pat. Nos. 5,202,238; and 5,204,244).

The humanized antibody of the present invention may be produced by obtaining nucleic acid sequences encoding CDR domains, as previously described, constructing a humanized antibody expression vector by inserting them into an expression vector for animal cell having genes encoding (i) a heavy chain constant region identical to that of a human antibody and (ii) a light chain constant region identical to that of a human antibody, and expressing the genes by introducing the expression vector into an animal cell. The humanized antibody expression vector may be either of a type in which a gene encoding an antibody heavy chain and a gene encoding an antibody light chain exists on separate vectors or of a type in which both genes exist on the same vector (tandem type). In respect of easiness of construction of a humanized antibody expression vector, easiness of introduction into animal cells, and balance between the expression levels of antibody H and L chains in animal cells, humanized antibody expression vector of the tandem type is preferred. Examples of tandem type humanized antibody expression vector include pKANTEX93 (WO 97/10354), pEE18 and the like. Methods for producing humanized antibodies based on conventional recombinant DNA and gene transfection techniques are well known in the art (See, e.g., Riechmann L. et al. 1988; Neuberger M S. et al. 1985). Antibodies can be humanized using a variety of techniques known in the art including, for example, CDR-grafting (EP 239,400; PCT publication WO91/09967; U.S. Pat. Nos. 5,225,539; 5,530,101; and 5,585,089), veneering or resurfacing (EP 592,106; EP 519,596; Padlan E A (1991); Studnicka G M et al. (1994); Roguska M A. et al. (1994)), and chain shuffling (U.S. Pat. No. 5,565,332). The general recombinant DNA technology for preparation of such antibodies is also known (see European Patent Application EP 125023 and International Patent Application WO 96/02576).

The Fab of the present invention can be obtained by treating an antibody which specifically reacts with AMH with a protease, papaine. Also, the Fab can be produced by inserting DNA encoding Fab of the antibody into a vector for prokaryotic expression system, or for eukaryotic expression system, and introducing the vector into a prokaryote or eucaryote (as appropriate) to express the Fab.

The F(ab')2 of the present invention can be obtained treating an antibody which specifically reacts with AMH with a protease, pepsin. Also, the F(ab')2 can be produced by binding Fab' described below via a thioether bond or a disulfide bond.

The Fab' of the present invention can be obtained treating F(ab')2 which specifically reacts with AMH with a reducing agent, dithiothreitol. Also, the Fab' can be produced by inserting DNA encoding Fab' fragment of the antibody into an expression vector for prokaryote, or an expression vector for eukaryote, and introducing the vector into a prokaryote or eukaryote (as appropriate) to perform its expression.

The scFv of the present invention can be produced by obtaining cDNA encoding the VH and VL domains as previously described, constructing DNA encoding scFv, inserting the DNA into an expression vector for prokaryote, or an expression vector for eukaryote, and then introducing the expression vector into a prokaryote or eukaryote (as appropriate) to express the scFv. To generate a humanized scFv fragment, a well-known technology called CDR grafting may be used, which involves selecting the complementary determining regions (CDRs) from a donor scFv fragment, and grafting them onto a human scFv fragment framework of known three dimensional structure (see, e.g., WO98/45322; WO 87/02671; U.S. Pat. Nos. 5,859,205; 5,585,089; 4,816,567; EP0173494).

Amino acid sequence modification(s) of the antibodies described herein are contemplated. For example, it may be desirable to improve the binding affinity and/or other biological properties of the antibody. It is known that when a humanized antibody is produced by simply grafting only CDRs in VH and VL of an antibody derived from a non-human animal in FRs of the VH and VL of a human antibody, the antigen binding activity is reduced in comparison with that of the original antibody derived from a non-human animal. It is considered that several amino acid residues of the VH and VL of the non-human antibody, not only in CDRs but also in FRs, are directly or indirectly associated with the antigen binding activity. Hence, substitution of these amino acid residues with different amino acid residues derived from FRs of the VH and VL of the human antibody would reduce of the binding activity. In order to resolve the problem, in antibodies grafted with human CDR, attempts have to be made to identify, among amino acid sequences of the FR of the VH and VL of human antibodies, an amino acid residue which is directly associated with binding to the antibody, or which interacts with an amino acid residue of CDR, or which maintains the three-dimensional structure of the antibody and which is directly associated with binding to the antigen. The reduced antigen binding activity could be increased by replacing the identified amino acids with amino acid residues of the original antibody derived from a non-human animal. Modifications and changes may be made in the structure of the antibodies of the present invention, and in the DNA sequences encoding them, and still obtain a functional molecule that encodes an antibody with desirable characteristics. In making the changes in the amino sequences, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). For example, certain amino acids may be substituted by other amino acids in a protein structure without appreciable loss of activity. Since the interactive capacity and nature of a protein define the protein's biological functional activity, certain amino acid substitutions can be made in a protein sequence, and, of course, in its DNA encoding sequence, while nevertheless obtaining a protein with like properties. It is thus contemplated that various changes may be made in the antibodies sequences of the invention, or corresponding DNA sequences which encode said antibodies, without appreciable loss of their biological activity. It is known in the art that certain amino acids may be substituted by other amino acids having a similar hydropathic index or score and still result in a protein with similar biological activity, i.e. still obtain a biological functionally equivalent protein. As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine. Said antibodies may be assayed for specific binding by any method known in the art. Many different competitive binding assay format(s) can be used for epitope binning. The immunoassays which can be used include, but are not limited to, competitive assay systems using techniques such western blots, radioimmunoassays, ELISA, "sandwich" immunoassays, immunoprecipitation assays, precipitin assays, gel diffusion precipitin assays, immunoradiometric assays, fluorescent immunoassays, protein A immunoassays, and complement-fixation assays. Such assays are routine and well known in the art (see, e.g., Ausubel et al., eds, 1994 Current Protocols in Molecular Biology, Vol. 1, John Wiley & sons, Inc., New York). For example, the BIACORE® (GE Healthcare, Piscataway, N.J.) is one of a variety of surface plasmon resonance assay formats that are routinely used to epitope bin panels of monoclonal antibodies. Additionally, routine cross-blocking assays such as those described in Antibodies, A Laboratory Manual, Cold Spring Harbor Laboratory, Ed Harlow and David Lane, 1988, can be performed.

Engineered antibodies of the present invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed by the invention. Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the present invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the present invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat. In some embodiments, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody. In some embodiments, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al. In some embodiments, the antibody is modified to increase its biological half-life. Various approaches are possible. For example, one or more of the following mutations can be introduced: T252L, T254S, T256F, as described in U.S. Pat. No. 6,277,375 by Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. In some embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al. In some embodiments, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al. In some embodiments, one or more amino acid residues are altered to thereby alter the ability of the antibody to fix complement. This approach is described further in PCT Publication WO 94/29351 by Bodmer et al. In some embodiments, the Fc region is modified to increase the ability of the antibody to mediate antibody dependent cellular cytotoxicity (ADCC) and/or to increase the affinity of the antibody for an Fc receptor by modifying one or more amino acids. This approach is described further in PCT Publication WO 00/42072 by Presta. Moreover, the binding sites on human IgG1 for FcγRI, FcγRII, FcγRIII and FcRn have been mapped and variants with improved binding have been described (see Shields, R. L. et al., 2001 J. Biol. Chen. 276:6591-6604, WO2010106180). In some embodiments, the glycosylation of an antibody is modified. For example, an aglycoslated antibody can be made (i.e., the antibody lacks glycosylation). Glycosylation can be altered to, for example, increase the affinity of the antibody for the antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al. Additionally or alternatively, an antibody can be made that has an altered type of glycosylation, such as a hypofucosylated or non-fucosylated antibody having reduced amounts of or no fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the present invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation or are devoid of fucosyl residues. Therefore, in some embodiments, the antibodies of the present invention may be produced by recombinant expression in a cell line which exhibit hypofucosylation or non-fucosylation pattern, for example, a mammalian cell line with deficient expression of the FUT8 gene encoding fucosyltransferase. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al., 2002 J. Biol. Chem. 277: 26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180). Eureka Therapeutics further describes genetically engineered CHO mammalian cells capable of producing antibodies with altered mammalian glycosylation pattern devoid of fucosyl residues (http://www.eurekainc.com/a&boutus/companyoverview.html). Alternatively, the antibodies of the present invention can be produced in yeasts or filamentous fungi engineered for mammalian-like glycosylation pattern and capable of producing antibodies lacking fucose as glycosylation pattern (see for example EP1297172B1).

Another modification of the antibodies herein that is contemplated by the invention is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the present invention. See for example, EP 0 154 316 by Nishimura et al. and EP 0 401 384 by Ishikawa et al.

The antibody of the invention may find various applications, notably in the field of reproductive medicine.

In some embodiments, the antibody of the present invention is particularly suitable for the improving folliculogenesis. In particular, the antibody of the present invention is suitable for improving follicle recruitment and response of antral follicles to controlled ovarian hyperstimulation. For instance, the antibody of the present invention is suitable for improving controlled ovarian hyperstimulation success rate. Typically, the antibody of the present invention exerts its effect by increasing the recruitment of primordial follicles, but also by increasing FSH sensitivity of the follicles. Accordingly treatments with the antibody of the present invention represent an adjunct to controlled ovarian hyperstimulation. Typically, controlled ovarian hyperstimulation (COH) consists in the administration of one active ingredient selected from the group consisting of GnRH agonists or antagonists associated with recombinant follicle-stimulating hormone (FSH) or human Chorionic Gonadotropin (hCGH). The antibody of the present invention is typically administered in combination GnRH agonists or antagonists, recombinant follicle-stimulating hormone (FSH) or human Chorionic Gonadotropin (hCGH).

In some embodiments, the present invention relates to a method of treating a female subject with diminished ovarian reserve or who poorly responds to controlled ovarian hyperstimulation comprising administering to the female subject a therapeutically effective amount of the antibody of the present invention. In some embodiments, the methods of treatment of the present invention comprises the steps consisting of i) determining the level of AMH in a blood sample obtained from the subject, ii) comparing the level determined at step i) with a predetermined reference value and ii) administering to the subject a therapeutically effective amount of the antibody of the present invention when the level determined at step i) is higher than the predetermined reference value.

In some embodiments, the antibody of the present invention is particularly suitable for the treatment of disorders characterized by follicle excess and arrest. In particular the antibody of the present invention is particularly suitable for the treatment of polycystic ovary syndrome (PCOS).

The antibody of the present inventions may also find application in techniques of fertility-preservation in patients with cancer based on ovarian tissue cryopreservation. In particular, it could help the development of the follicles contained in an ovarian biopsy (in vitro folliculogeneis technology) before its graft in woman who had a cancer treatment. In some embodiments, the antibody of the present invention is particularly suitable for improving in vitro folliculogenesis.

Typically the antibody of the present invention is administered to the subject in an effective amount, i.e. an amount that is sufficient to fulfill its intended purpose. The exact amount of the antibody of the present invention to be administered will vary from subject to subject, depending on the age, sex, weight and general health condition of the subject to be treated, the desired biological or medical response. Accordingly, the term "therapeutically effective amount" refers to an amount effective, at dosages and for periods of time necessary, to achieve a desired therapeutic result. A therapeutically effective amount of the antibody of the present invention may vary according to factors such as the disease state, age, sex, and weight of the individual, and the ability of the antibody of the present invention to elicit a desired response in the individual. A therapeutically effective amount is also one in which any toxic or detrimental effects of the antibody or antibody portion are outweighed by the therapeutically beneficial effects. The efficient dosages and dosage regimens for the antibody of the present invention depend on the disease or condition to be treated and may be determined by the persons skilled in the art. A physician having ordinary skill in the art may readily determine and prescribe the effective amount of the pharmaceutical composition required. For example, the physician could start doses of the antibody of the present invention employed in the pharmaceutical composition at levels lower than that required in order to achieve the desired therapeutic effect and gradually increase the dosage until the desired effect is achieved. In general, a suitable dose of a composition of the present invention will be that amount of the compound which is the lowest dose effective to produce a therapeutic effect according to a particular dosage regimen. Such an effective dose will generally depend upon the factors described above. For example, a therapeutically effective amount for therapeutic use may be measured by its ability to stabilize the progression of disease. An exemplary, non-limiting range for a therapeutically effective amount of an antibody of the present invention is about 0.1-100 mg/kg, such as about 0.1-50 mg/kg, for example about 0.1-20 mg/kg, such as about 0.1-10 mg/kg, for instance about 0.5, about such as 0.3, about 1, about 3 mg/kg, about 5 mg/kg or about 8 mg/kg. An exemplary, non-limiting range for a therapeutically effective amount of an antibody of the present invention is 0.02-100 mg/kg, such as about 0.02-30 mg/kg, such as about 0.05-10 mg/kg or 0.1-3 mg/kg, for example about 0.5-2 mg/kg. Administration may e.g. be intravenous, intramuscular, intraperitoneal, or subcutaneous, and for instance administered proximal to the site of the target. Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. If desired, an effective daily dose of a pharmaceutical composition may be administered as two, three, four, five, six or more sub-doses administered separately at appropriate intervals throughout the day, optionally, in unit dosage forms. In some embodiments, the antibodies of the present invention are administered by slow continuous infusion over a long period, such as more than 24 hours, in order to minimize any unwanted side effects. An effective dose of an antibody of the present invention may also be administered using a weekly, biweekly or triweekly dosing period. The dosing period may be restricted to, e.g., 8 weeks, 12 weeks or until clinical progression has been established. As non-limiting examples, treatment according to the present invention may be provided as a daily dosage of a compound of the present invention in an amount of about 0.1-100 mg/kg, such as 0.2, 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of days 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of weeks 1, 2, 3, 4, 5, 6, 7, 8, 9, 10, 11, 12, 13, 14, 15, 16, 17, 18, 19 or 20 after initiation of treatment, or any combination thereof, using single or divided doses every 24, 12, 8, 6, 4, or 2 hours, or any combination thereof.

For administration, the antibody of the present invention is formulated as a pharmaceutical composition. A pharmaceutical composition comprising an antibody of the present invention can be formulated according to known methods to prepare pharmaceutically useful compositions, whereby the therapeutic molecule is combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. (See, e.g., Gennaro (ed.), Remington's Pharmaceutical Sciences (Mack Publishing Company, 19th ed. 1995)) Formulations may further include one or more excipients, preservatives, solubilizers, buffering agents, albumin to prevent protein loss on vial surfaces, etc. The form of the pharmaceutical compositions, the route of administration, the dosage and the regimen naturally depend upon the condition to be treated, the severity of the illness, the age, weight, and sex of the patient, etc. The pharmaceutical compositions of the present invention can be formulated for a topical, oral, parenteral, intranasal, intravenous, intramuscular, subcutaneous or intraocular administration and the like. Typically, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. To prepare pharmaceutical compositions, an effective amount of the antibody of the present invention may be dissolved or dispersed in a pharmaceutically acceptable carrier or aqueous medium. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. An antibody of the present invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The preparation of more, or highly concentrated solutions for direct injection is also contemplated, where the use of DMSO as solvent is envisioned to result in extremely rapid penetration, delivering high concentrations of the active agents to a small tumor area. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The invention will be further illustrated by the following figures and examples. However, these examples and figures should not be interpreted in any way as limiting the scope of the present invention.

FIGURES

FIG. 1: Effects of AMH mAbs on AMH induced Smad Phosphorylation in SMAT1 cells. mAb 22A2 blocks AMH induced Smad phosphorylation in SMAT1 cells, but mAb 10.6 has no effect. Cleaved- or C-terminal AMH (8 nM) was preincubated with mAbs 10.6 or 22A2 (50 µg/ml) for 1 h at room temperature prior to exposure to SMAT1 cells for 30 min. Phospho-Smad1/5/8 and tubulin levels were assessed by Western blotting of cell lysates. The heavy chains of mAbs 10.6 and 22A2 were detected by the secondary antibody used for the tubulin analysis. A quantitation of Smad phosphorylation levels are shown on the right.

Figure 2A:
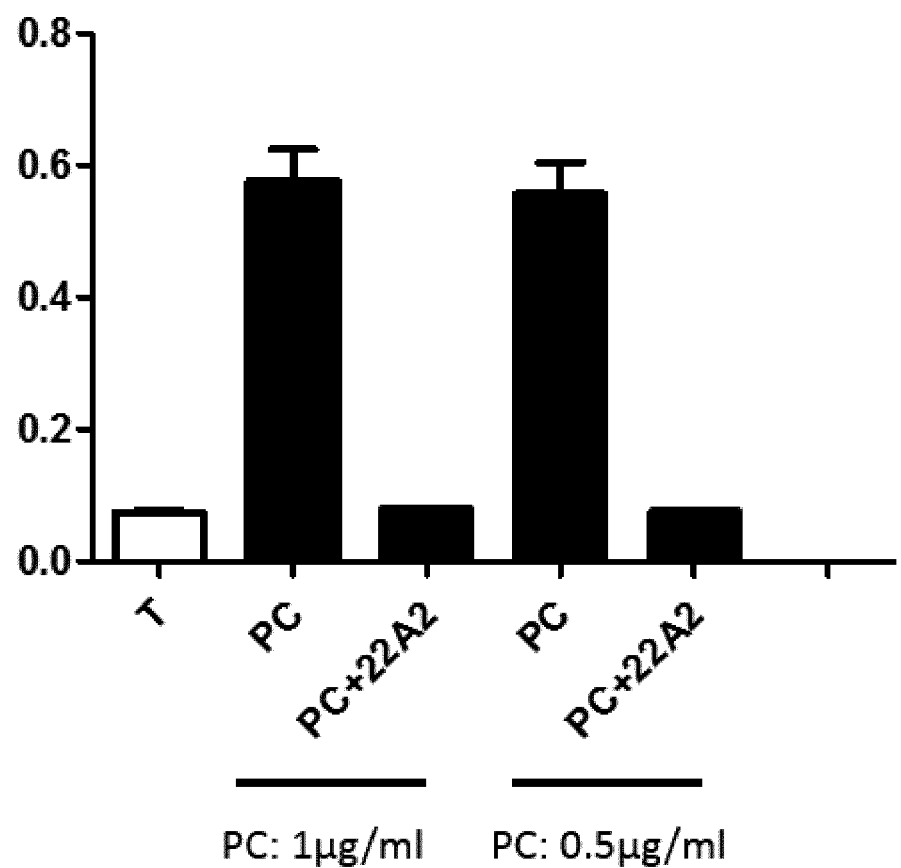
Figure 2B:
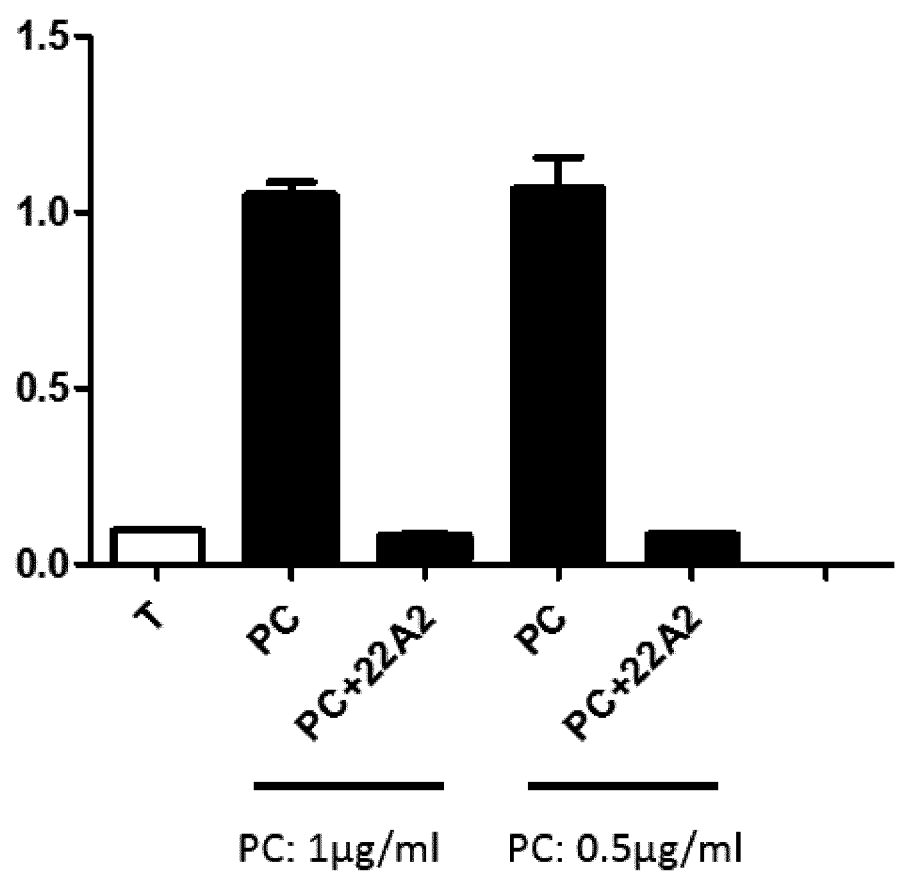

FIG. 2: Quantification of the effects of AMH mAbs.

A. Smad1 reporter construct; B. Smad5 reporter construct.

Figure 3:
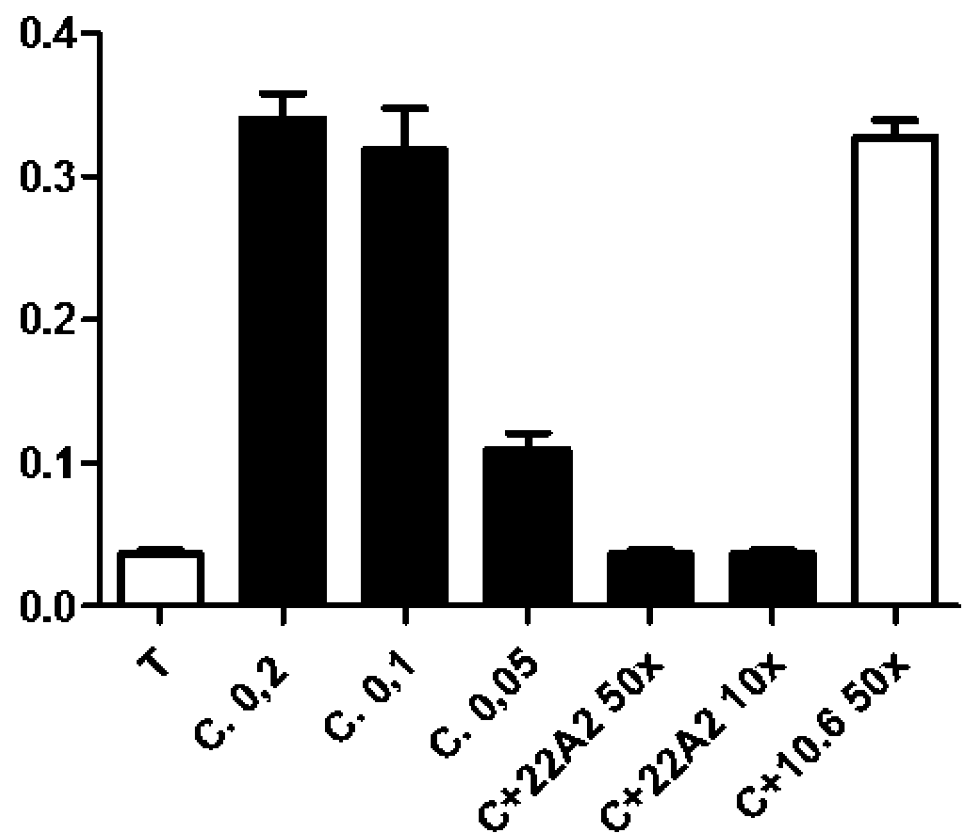

FIG. 3: The functional activation of Smad1, 5, 8 pathway was assessed by a reporter system composed of a Gal4-Smad5 fusion proteins and a Gal4-luc reporter construct.

EXAMPLE 1

Methods:

Cleaved AMH and C-terminal AMH {di Clemente, 2010 #880} and anti-AMH mAbs 22A2 and 10.6 {Long, 2000 #813; Wilson, 1993 #50} were previously described. Smad phosphorylation was determined as previously described {Gouédard, 2000 #274}. Briefly, SMAT1 cells were seeded into 6 well tissue culture plates at approximately 50% density in Dulbecco's modified Eagle's medium containing 10% fetal bovine serum (FBS), 100 U/ml penicillin, and 100 µg/ml streptomycin (Life Technologies, Rockville, Md.). The next day the cells were washed, medium without serum was added for 1 h, and then AMH was added in culture medium without serum for 30 min. The cells were washed and solubilized in 200 µl of lysis buffer (20 mM Tris-HCl, pH 7.5, 150 mM NaCl, 1% (V/V) Triton X-100) containing 1 mM phenylmethylsulfonyl fluoride, a proteinase inhibitor mixture (Sigma-Aldrich, St Louis, Mo.) and a phosphatase inhibitor cocktail (Calbiochem Merck Biosciences, Darmstadt, Germany). The lysates were cleared by centrifugation and supernatants were analyzed by SDS-PAGE followed by western blotting with a rabbit anti-phosphoSmad1, 5 mAb (Cell Signaling; 1:1000 dilution) and a goat anti-rabbit IgG antibody conjugated to HRP (Jackson ImmunoResearch Laboratories; 1:5000 dilution). The membranes were stripped and reprobed with a mouse anti-tubulin mAb (clone B-5-1-2, Sigma-Aldrich, St. Louis, Mo.).

To assess the effects of the anti-AMH mAbs on AMH induced Smad phosphorylation, cleaved AMH (at 1 µg/ml) or C-terminal AMH (at 0.2 µg/ml) were incubated for 1 hour with either mAb 10.6 or 22A2 (at 50 µg/ml) at room temperature for 60 min in culture medium. The culture medium containing the AMH and mAbs was then added to the cells as described above. Controls without AMH or without mAbs were also performed.

Results

SMAT-1 cells, an immature mouse Sertoli cell line, expresses AMHRII and all three type I receptors and can respond to AMH, as evident by the phosphorylation of Smad1/5/8 proteins, which represents the first step in intracellular signaling by AMH. To investigate the effect of AMH mAbs on Smad phosphorylation, SMAT1 cells were treated with cleaved-AMH or C-terminal AMH after preincubation with mAbs 10.6 or 22A2, and cell lysates were then subjected to Western analysis using an anti phospho-Smad1/5/8 antibody. C-terminal AMH was purified from cleaved-AMH and contains 100% mature C-terminal homodimer. Preincubation of cleaved-AMH or C-terminal AMH with mAb 10.6 did not affect their ability to induce Smad phosphorylation in SMAT-1 cells (Figure). In contrast, preincubation of mAb 22A2 with cleaved-AMH or C-terminal AMH completely blocked Smad phosphorylation induced by both AMH proteins (FIG. 1).

The ability of mAb 22A2 to block Smad phosphorylation indicates that it can block the assembly of an active receptor signaling complex. However, previously, we have shown that mAb 22A2 cannot block binding of cleaved AMH to the soluble type II receptor, AMHRII-Fc. This strongly implies that when cleaved or C-terminal AMH is bound to mAb 22A2, it cannot bind the type I receptor. There is evidence that the epitope for mAb 22A2 on the C-terminal domain is located close to the type I receptor binding site. mAb 22A2 does not recognize mouse AMH, indicating that the mAb 22A2 epitope must be in a region where there are differences between the mouse and human AMH proteins. There are only 8 amino acid differences within the C-terminal domain; three of these are at the N-terminus of the C-terminal domain and the other five are close to or within the pre-helix loop (2) or α-helix (3), two features that are part of the wrist epitope, the putative binding site for the type I receptor. The epitope for Mab 22A2 is likely to be in the wrist epitope region, since the N-termini of TGF-β mature domains tend to have less structure and have no contact with either the type I or type II receptors.

EXAMPLE 2

Methods:

SMAT-1 cells seeded in 24-wells plates at 7.5×104 cells per well. 24 h later, cells were co-transfected using lipofectamine Plus reagent with either Gal4-Smad1 or Gal4-Smad5 (250 ng) and Gal4-luc (250 ng) plasmids, and 12.5 ng of pRLTK as a control for transfection efficiency. After the transfection, cells were treated with either control medium, plasmin-cleaved AMH (0.5 or 1 µg/ml), or plasmin-cleaved AMH pre-incubated 1 h in presence of a 50 fold excess of Mab 22A2 (25 or 50 µg/ml). 24 h later, cells were washed twice with PBS, and lysed for 20 min under rocking in 125 µl of passive lysis buffer (Promega, Madison, Wis.) per well. Twenty µl were analysed for Firefly and *Renilla* luciferase activity according to the manufacturer (Dual Luciferase kit, Promega) using a TriStar luminometer (Berthold). Results were expressed as a ratio of Firefly to *Renilla* luciferase activity. Data are a mean±SEM of 1 experiment, done in quadriplate.

Results:

The functional activation of Smad1 pathway was assessed by a reporter system composed of Gal4-Smad1 or a Gal4-Smad5 fusion proteins and a Gal4-luc reporter construct (Clarke et al., 2001). Both concentrations of plasmin-cleaved AMH induce a 10-fold stimulation of Smad1 and Smad5 reporter systems, which is abolished by a 50-fold excess of 22A2.

EXAMPLE 3

Methods:

SMAT-1 cells seeded in 24-wells plates at 7.5×104 cells per well. 24 h later, cells were co-transfected using lipofectamine Plus reagent with Gal4-Smad5 (250 ng) and Gal4-luc (250 ng) plasmids, and 12.5 ng of pRLTK as a control for transfection efficiency. After the transfection, cells were treated with either control medium, C-terminal AMH (0.2 to 0.05 µg/ml), or C-terminal AMH (0.2 µg/ml) pre-incubated 1 h in presence of a 50-fold or 10-fold excess of Mab 22A2, or a 50-fold excess of Mab 10.6. 24 h later, cells were washed twice with PBS, and lysed for 20 min under rocking in 125 µl of passive lysis buffer (Promega, Madison, Wis.) per well. Twenty µl were analysed for Firefly and *Renilla* luciferase activity according to the manufacturer (Dual Luciferase kit, Promega) using a TriStar luminometer (Berthold). Results were expressed as a ratio of Firefly to *Renilla* luciferase activity. Data are a mean±SEM of 1 experiment, done in quadriplate.

Results:

The functional activation of Smad1, 5, 8 pathway was assessed by a reporter system composed of a Gal4-Smad5 fusion proteins and a Gal4-luc reporter construct (Clarke et al., 2001). C-terminal AMH induce a 10-fold stimulation of Smad5 reporter system, which is abolished by both a 50-fold and a 10-fold excess of 22A2, but not by a 50-fold excess of 10.6.

REFERENCES

Throughout this application, various references describe the state of the art to which this invention pertains. The disclosures of these references are hereby incorporated by reference into the present disclosure.

The invention claimed is:

1. A method of improving folliculogenesis in a female subject comprising administering to the female subject a therapeutically effective amount of an Anti-Mullerian Hormone (AMH) neutralizing antibody which comprises a heavy chain comprising the H-CDR1, H-CDR2 and H-CDR3 of the heavy chain of the antibody obtainable from the hybridoma available under CNCM deposit number I-4965 and a light chain comprising the L-CDR1, L-CDR2 and L-CDR3 of the light chain of the antibody obtainable from the hybridoma available under CNCM deposit number I-4965.

2. The method of claim 1, wherein the female subject has diminished ovarian reserve or responds poorly to controlled ovarian hyperstimulation.

3. The method of claim 1 which comprises the steps of i) determining the level of AMH in a blood sample obtained from the subject, ii) comparing the level determined at step i) with a predetermined reference value and iii) administering to the subject a therapeutically effective amount of the AMH neutralizing antibody when the level determined at step i) is higher than the predetermined reference value.

4. The method of claim 1 wherein the AMH neutralizing antibody comprises the heavy chain of the antibody obtainable from the hybridoma available under CNCM deposit number I-4965 and the light chain of the antibody obtainable from the hybridoma available under CNCM deposit number I-4965.

5. The method of claim 1 wherein the AMH neutralizing antibody is a murine antibody.

6. The method of claim 5 wherein the murine antibody is obtainable from the hybridoma available under CNCM deposit number I-4965.

7. The method of claim 1 wherein the AMH neutralizing antibody is a chimeric antibody.

8. The method of claim 7 wherein the chimeric antibody is a mouse/human antibody.

9. The method of claim 1, wherein the AMH neutralizing antibody is a humanized antibody.

10. The method of claim 1 wherein the AMH neutralizing antibody is selected from the group of Fab, F(ab')2, Fab' and scFv.

11. The method of claim 1, wherein the method is performed as an adjunct to controlled ovarian hyperstimulation (COH).

12. The method of claim 11, wherein the controlled ovarian hyperstimulation comprises administration of a GnRH agonist or antagonist, recombinant follicle-stimulating hormone (FSH) or human Chorionic Gonadotropin (hCGH).

13. A method of treating polycystic ovary syndrome (PCOS) in a subject in need thereof comprising administering to the subject a therapeutically effective amount of an Anti-Mullerian Hormone (AMH) neutralizing antibody which comprises a heavy chain comprising the H-CDR1, H-CDR2 and H-CDR3 of the heavy chain of the antibody obtainable from the hybridoma available under CNCM deposit number I-4965 and a light chain comprising the L-CDR1, L-CDR2 and L-CDR3 of the light chain of the antibody obtainable from the hybridoma available under CNCM deposit number I-4965.

* * * * *